United States Patent [19]

Daughenbaugh et al.

[11] 4,417,074

[45] Nov. 22, 1983

[54] ALLYLAMINES FROM ALLYL ALCOHOL

[75] Inventors: Randall J. Daughenbaugh, Longmont, Colo.; Dale D. Dixon, Kutztown, Pa.

[73] Assignee: Air Products and Chemicals, Inc., Allentown, Pa.

[21] Appl. No.: 313,895

[22] Filed: Oct. 22, 1981

[51] Int. Cl.³ .............................................. C07C 85/06
[52] U.S. Cl. .................................................... 564/479
[58] Field of Search ........................................ 564/479

[56] References Cited

U.S. PATENT DOCUMENTS

| | | | |
|---|---|---|---|
| 1,992,935 | 3/1935 | Arnold | 564/479 |
| 2,073,671 | 3/1937 | Andrews | 564/479 |
| 2,082,105 | 6/1937 | Herold et al. | 564/479 |
| 2,113,241 | 4/1938 | Punnett | 564/479 |
| 2,216,548 | 8/1940 | Converse | 260/585 |
| 2,603,645 | 7/1952 | Hoog et al. | 260/290 |
| 2,605,264 | 7/1952 | Hoog et al. | 260/290 |
| 3,110,731 | 11/1963 | Boswell | 260/583 |
| 3,175,009 | 3/1965 | Koski et al. | 260/585 |
| 3,428,685 | 2/1969 | Hall | 260/585 |
| 3,475,344 | 10/1969 | Adam et al. | 564/479 X |
| 3,493,617 | 2/1970 | Shryne et al. | 260/583 |
| 3,865,877 | 2/1975 | Arpe et al. | 260/583 |
| 3,869,526 | 3/1975 | Combey et al. | 260/929 |
| 3,869,527 | 3/1975 | Hogberg et al. | 260/946 |
| 4,036,881 | 7/1977 | Brennan et al. | 260/583 |
| 4,044,053 | 8/1977 | Brennan et al. | 564/479 |
| 4,083,874 | 4/1978 | McConaghy | 260/585 |
| 4,103,087 | 7/1978 | Brennan | 564/479 X |

OTHER PUBLICATIONS

Research Disclosure 16906, p. 35, May 1978.

*Primary Examiner*—Paul F. Shaver
*Attorney, Agent, or Firm*—Michael Leach; E. Eugene Innis; James C. Simmons

[57] ABSTRACT

A process for preparing allylic amines which comprises contacting an allylic alcohol with ammonia or a primary or secondary amine in the presence of an effective amount of a phosphorus containing substance at a temperature sufficient to effect a reaction between the allylic alcohol and the ammonia or organic amine to produce an allylic amine.

17 Claims, No Drawings

4,417,074

ALLYLAMINES FROM ALLYL ALCOHOL

TECHNICAL FIELD

This invention relates to the preparation of allylic amines from allylic alcohols.

BACKGROUND OF THE PRIOR ART

At present, the main route to the allylamines is probably the reaction of an allyl halide with ammonia. This reaction can take place both in the vapor and the liquid phases as represented by U.S. Pat. Nos. 2,216,548 and 3,175,009. The mix of mono-, di-, and triallylamines is hard to control when using an allyl halide with tertiary and even quaternary amines being the main products. Moreover, the product is an amine hydrohalide which must be neutralized with base to recover the free amine. This recovery scheme produces a corrosive by-product stream of a halide salt for disposal.

It is also known to convert the triallylamine by-product resulting from the allyl halide-ammonia reaction into diallylamine. U.S. Pat. No. 3,428,685 discloses the pyrolysis of triallylamine hydrochloride, resulting in a mixture of diallylamine and allyl chloride. U.S. Pat. No. 3,110,731 discloses a catalytic process for converting triallylamine to diallylamine in the presence of a hydrogenation catalyst such as palladium.

The allylation of nitrogen compounds containing an active hydrogen using allyl ethers and esters is known to be catalyzed by palladium complexes. U.S. Pat. No. 3,493,617 discloses the production of N-allyl substituted secondary or tertiary organic amines by reacting an allylic aryl ether or an allylic carboxylate ester of an organic carboxylic acid with an organic amine in the presence of certain metal compounds containing organic complexing ligands, the metal being palladium, platinum or rhodium and the ligands being phosphines. U.S. Pat. No. 4,083,874 discloses a process for the production of allylic amines which comprises reacting a pi-allyl palladium complex with ammonia or an amine having a reactive hydrogen attached to the nitrogen atom and a cupric salt, the palladium being stabilized by a ligand material having the formula $R_3M$, wherein M is phosphorus, arsenic, antimony or bismuth and R is a hydrocarbyl or hydrocarbyloxy group. It is also known that a complex of palladium and triphenyl phosphine or tributyl phosphine can be used for the disproportionation of diallylamines to the corresponding mono- and triallylamines. See U.S. Pat. No. 3,865,877.

*Research Disclosure*, 16906, p. 35, May 1978 discloses that allyl compounds such as allyl acetate, allyl chloride, allyl cyanide, allyl ether and allyl alcohol can be converted to allylamines by reacting the allyl compounds with a dialkylamine or ammonium salt of a carboxylic acid. Catalysts suitable for these reactions are those comprising a zero valent complex of metals such as palladium, platinum, ruthenium, nickel and cobalt bearing phosphorus organo containing ligands.

However, reacting allyl alcohol in the presence of an alumina and copper catalyst yields primarily beta-picoline. See U.S. Pat. Nos. 2,603,645 and 2,605,264.

SUMMARY OF THE INVENTION

Broadly, we have discovered that allylic amines can be prepared by:

(a) contacting an allylic alcohol of the formula $CH_2=C(R)-CH_2OH$ wherein R is hydrogen or methyl with ammonia or an organic amine of the formula $R_1R_2NH$ wherein $R_1$ and $R_2$ represent hydrogen or a lower $C_1$-$C_5$ hydrocarbyl group in the presence of an effective amount of a phosphorus containing substance at a temperature sufficient to effect a reaction between the allylic alcohol and the ammonia or amine to produce an allylic amine, and (b) recovering the allylic amine.

The reaction of the allylic alcohol with ammonia or the organic amine may take place as a liquid phase or a gas phase reaction with the latter being more desirable.

An advantage of the invention is the absence of a corrosive by-product stream of halide salt since the process is relatively clean affording water as the major by-product.

As another advantage, the products may be readily recovered by simple distillation steps.

Yet another advantage is that the product distribution is flexible and easily controlled to an extent by recycling of the less desired allylic amines.

DETAILED DESCRIPTION OF THE INVENTION

The invention relates to a process for synthesizing allylic amines, particularly allylamines and methallylamines. In the process an allylic alcohol having the formula $CH_2=C(R)-CH_2OH$ wherein R is hydrogen or methyl is contacted with ammonia or a primary or secondary amine of the formula $R_1R_2NH$ wherein $R_1$ and $R_2$ represent hydrogen or a lower $C_1$-$C_5$ hydrocarbyl group. Examples of suitable hydrocarbyl groups include methyl, ethyl, n-propyl, isopropyl, n-butyl, isobutyl, n-pentyl, allyl, isopropenyl and the like. Preferred hydrocarbyl groups are methyl, ethyl and allyl. Contemplated as functional equivalents of ammonia and the organic amines used in the process of this invention are the corresponding ammonium and amine salts of carboxylic acids and mineral acids such as the acetate, halide, sulfate and phosphate salts.

The reaction is conducted in the presence of an effective amount of a phosphorus containing substance at a temperature sufficient to effect a reaction between the allylic alcohol and the ammonia or organic amine to produce an allylic amine. Such temperatures may range from about 0° to 400° C., preferably from about 150° to 350° C.

The reaction of this invention may take place as a gas phase reaction or a liquid phase reaction. Temperatures from about 150° to 350° C. and pressures from about 1 to 100 atmospheres may be used when performing gas phase reactions. The pressure utilized to carry out liquid phase reactions is that autogenous pressure which is sufficient to maintain the reaction in essentially liquid phase although higher pressures may be used. Liquid phase reaction temperatures may range from about 0° to 300° C. When utilizing these temperatures and pressures, the reaction is allowed to proceed until a desired conversion is obtained or the reaction is complete.

The catalysts which are suited for practicing the process described herein are the phosphorus containing substances disclosed in U.S. Pat. No. 4,036,881 which is incorporated by reference. Suitable phosphorus containing substances include, for example, acidic metal phosphates, phosphoric acid compounds and their anhydrides, phosphorous acid compounds and their anhydrides, alkyl or aryl phosphate esters, alkyl or aryl phosphite esters, alkyl or aryl substituted phosphorous acids and phosphoric acids, wherein the alkyl groups have from 1 to about 8 carbon atoms and the aryl groups have from about 6 to about 20 carbon atoms, alkali metal monosalts of phosphoric acid and mixtures of any of the above.

More particularly, suitable acidic metal phosphates include boron phosphate, ferric phosphate, aluminum phosphate, and the like.

Suitable phosphoric acid compounds include aqueous or anhydrous phosphoric acids such as orthophosphoric acid, pyrophosphoric acid, metaphosphoric acid, and condensed phosphoric acids such as polyphosphoric acids. Accordingly, an example of a suitable phosphoric acid is orthophosphoric acid.

In addition, any commercially available mono-, di-, or trialkyl or aryl phosphate or phosphite ester can be employed as the catalyst in the inventive process. Additionally, bis(phosphates) and secondary phosphate esters such as those disclosed in U.S. Pat. Nos. 3,869,526 and 3,869,527, respectively, can be used. Preferably, the lower alkyl esters are employed such as those having from 1 to about 8 carbon atoms per alkyl group. Preferred aryl esters contain from about 6 to about 20 carbon atoms may include a phenyl group or alkyl-substituted phenyl group.

Further, suitable alkyl or aryl substituted phosphoric acids or phosphorous acids which may be employed as a catalyst include alkyl phosphonic acids, aryl phosphonic acids, alkyl phosphinic acids and aryl phosphinic acids. Preferably, such acids include alkyl or aryl groups and have from 1 to about 8 carbon atoms in each alkyl group and from about 6 to about 20 carbon atoms in each aryl group.

Specific examples of alkyl and aryl substituted phosphorous and phosphoric acids that may be used in accordance with the invention are phenylphosphinic, ethylphosphonic, phenylphosphonic, naphthaphosphonic, and methylphosphinic acids. Examples of the alkyl and aryl substituted phosphorous and phosphoric acid esters are methylphenyl phosphonate, dimethylphenyl phosphonate, methylphenyl phosphinate, ethylnaphthaphosphinate, and propylmethyl phosphonate.

It should be noted that the phosphorus containing substances according to this invention do not include metal catalysts, such as palladium, platinum, rhodium, ruthenium, nickel or cobalt, bearing phosphorus containing ligands.

The above mentioned phosphorus compounds are not intended to be exhaustive of those which may be employed as a catalyst material in the process of the present invention. Those materials are set forth to specify types of phosphorus compounds that a worker in the art may use as a catalyst material. It is especially preferred to use those that have been found to be most reactive under the processing conditions of the invention. These especially preferred compounds include boron phosphate and orthophosphoric acid.

The quantity of phosphorus containing substance used in the reaction is empirical and can vary widely depending upon the reactivity of the catalysts and the reactivity of the reactants present. An effective amount of a phosphorus containing substance is used; in other words, an amount which causes a reaction between the allylic alcohol and the ammonia or organic amine to yield an allylic amine at the temperature and pressure used. Usually, the amount of active phosphorus material used to provide a catalytic effect in bulk, or slurry, reactions ranges from about 0.05 to 10 mole % based upon the amount of the allylic alcohol present in the reaction mixture, and preferably in an amount from about 0.5 to 4 mole %. Within these ranges though, the level of catalyst again is empirical and is adjusted depending on the products that are desired since the allylic amines are generated in an equilibrium distribution.

For a continuous reaction using a fixed bed system in which the phosphorus containing substance is present on an inert support or in bulk form, suitable reaction temperatures can range from 150° to 350° C., preferably 200° to 300° C. and suitable pressures can range from 1 to 100 atmospheres, preferably 10 to 30 atmospheres. Flow rates which may be used, expressed as liquid hourly space velocity (LHSV), are from 0.1 to 4 hour$^{-1}$ based on allylic alcohol.

Generally, the mole ratio of ammonia or amine compound to allylic alcohol compound may range from about 1:3 to 40:1, and preferably is about 1:1 to 10:1. It is advantageous in carrying out the process of this invention that the proportion of ammonia or amine compound to the allylic alcohol compound be in a stoichiometric excess, e.g. from about 1:1 up to 20:1 to result in formation predominantly of the monoallylic amine. When the ammonia or amine compound approaches a 1:1 molar ratio with the allylic alcohol, or falls below that level, the formation of di- and triallylic amine compounds will predominate.

The process of the invention can be carried out batchwise or continuously employing well known batch and continuous processing techniques and conventional processing apparatus. In such continuous reaction processes, the above described phosphorus containing materials may be employed as a feed stream alone or admixed with a reactant feed stream, or they may be employed as a fixed bed catalyst in the continuous reactor system. Generally speaking, these fixed bed catalysts comprise the phosphorus containing substance supported on a material, such as silica, silica-alumina, alumina, diatomaceous earth, etc., conventionally employed as an inert reactor packing material. Such fixed bed supported catalysts and procedures for their preparation are well known in the art and many are readily available commercially.

Recovery of the allylic amine products from the reaction mixture can be accomplished by conventional techniques, these techniques generally involving a fractionation step such as distillation. For example, the reaction product mass may be directly distilled or initially filtered to remove a small amount of formed solids which usually are amine salt complexes of the phosphorus containing material, and then distilled. The desired allylic amine compounds may then be separately collected in salt free form. This is an advantage over the prior art processes in which the allylic amine products had to be liberated from their corresponding mineral acid salts before they could be recovered.

In addition, a continuous process yielding an equilibrium product distribution permits the recycling of the less desirable allylic amines after a separation step.

The following examples which illustrate the nature of the process described herein are not intended to limit the scope of the invention.

EXAMPLE I

In this run, boron phosphate was shown effective as a catalyst for the production of allylamine from allyl alcohol. The catalyst was prepared by mixing 5.38 g of an 85% aqueous orthophosphoric acid solution (0.047 mole) and 2.89 g (0.047 mole) orthoboric acid. The resultant gel was dried in an oven and crushed. The catalyst was charged to a 300 cc stirred autoclave along with 100 ml allyl alcohol. After purging the autoclave with nitrogen gas, 16 ml liquid ammonia was charged. After stirring for 30 minutes at room temperature, the reaction was heated to 100° C. for 30 minutes, then to 200° C. for 30 minutes, and to 300° C. for 30 minutes. A sample was taken after the 30 minutes at each temperature and also after a total of 90 minutes at 300° C. These samples were analyzed by gas chromatography. Identification of products was by gas chromatography retention time only. Table I shows the relative amounts of the materials detected in the reaction samples based on gas chromatography area percentages at the various temperatures. The triallylamine (2.0%) which was detected in the 200° C. reaction sample was most likely an artifact since the samples at 300° C. showed only the mono- and diallylamines and no trisubstituted product.

TABLE I

| °C. | MAA | DAA | TAA | AAL | OTHER |
|---|---|---|---|---|---|
| RT | — | — | — | 83.7 | 16.3 |
| 100 | — | — | — | 91.3 | 8.7 |
| 200 | — | — | 2.0 | 94.9 | 3.1 |
| 300 | 0.15 | trace | — | 91.3 | 8.5 |
| 300 (90 min) | 0.24 | 0.17 | — | 89.9 | 9.7 |

MAA—monoallylamine
DAA—diallylamine
TAA—triallylamine
AAL—allyl alcohol

EXAMPLE II

In this run the catalyst used was orthophosphoric acid on a silica support in a continuous fixed bed-vapor phase reaction process. The catalyst [10 cc (6.68 g); 12/18 mesh], which was obtained from Davison Chemical of Baltimore, Maryland, comprised silica pills impregnated with orthophosphoric acid at 18.7 lb $H_3PO_4/ft^3$ (300 kg/m$^3$). Pressure was about 300 psig (21 atm). The feed stream ratio was about 8 moles ammonia to 1 mole allyl alcohol. The liquid hourly space velocity (LHSV) based on the alcohol was 0.5 hour$^{-1}$. As the temperature was raised, some allylamine (about 1.3%) was formed at about 195° C. Conversion increased with temperature to about 23% conversion at 320° C. Identification of products was by gas chromatography retention time and mass spectrometry. Table II shows the amounts of the materials detected in the reaction based on gas chromatography area percentages at various temperatures.

The yield to amines was about 87% for the 277° and 320° C. samples. No n-propylamines were observed.

TABLE II

| °C. | MAA | DAA | TAA | AAL | OTHER |
|---|---|---|---|---|---|
| 195 | 1.3 | — | — | 98.7 | — |
| 250 | 4.5 | trace | — | 95.5 | — |
| 277 | 9.4 | 0.3 | trace | 89 | 1.3 |
| 320 | 18.7 | 0.9 | 0.4 | 77 | 3 |

MAA—monallylamine
DAA—diallylamine
TAA—triallylamine
AAL—allyl alcohol

STATEMENT OF INDUSTRIAL APPLICATION

The invention provides a process for the preparation of allylamines from allyl alcohol. Salts of the allylamines are used in the synthesis of ion-exchange resins, water-dispersable copolymers useful for water purification, dewatering of sewage sludge, flocculation of mining muds and the preparation of electrically conductive papers.

We claim:

1. A process for preparing allylic amines comprising: contacting an allylic alcohol of the formula $CH_2=C(R)-CH_2OH$ wherein R is hydrogen or methyl with ammonia or an organic amine of the formula $R_1R_2NH$ wherein $R_1$ and $R_2$ represent hydrogen or a lower $C_1-C_5$ hydrocarbyl group in the presence of a catalytically effective amount of a phosphorus containing substance which is not a phosphorus containing ligand complexed with a metal at a temperature sufficient to effect a reaction between the allylic alcohol and the ammonia or organic amine to produce an allylic amine.

2. The process of claim 1 wherein the phosphorus containing substance is selected from the group consisting of acid metal phosphates, phosphoric acid compounds and their anhydrides, phosphorous acid compounds and their anhydrides, alkyl or aryl phosphate esters, alkyl or aryl phosphite esters, alkyl or aryl substituted phosphorous acids and phosphoric acids wherein the alkyl groups have from 1 to about 8 carbon atoms and the aryl groups have from 6 to about 20 carbon atoms, alkali metal monosalts of phosphoric acid and mixtures of the above.

3. The process of claims 1 or 2 wherein the phosphorus containing substance is present in an amount from about 0.05 to about 10 mole % based upon the amount of allylic alcohol present.

4. The process of claim 2 wherein the temperature is from about 0° to about 400° C.

5. The process of claim 4 wherein the temperature is from about 150° to 350° C.

6. The process of claim 4 wherein the ammonia or the organic amine and the allylic alcohol compound are contacted in a molar ratio of from about 1:1 to about 20:1.

7. The process of claim 4 wherein the reaction is conducted as a continuous process.

8. The process of claim 7 wherein the temperature is from about 150° to 350° C.

9. The process of claim 6 wherein the phosphorus containing substance is a phosphoric acid compound.

10. The process of claim 9 wherein the phosphorus containing substance is orthophosphoric acid.

11. The process of claim 6 wherein the phosphorus containing substance is an acidic metal phosphate.

12. The process of claim 11 wherein the phosphorus containing substance is boron phosphate.

13. The process of claims 1 or 2 wherein the allylic alcohol is contacted with ammonia.

14. A process for preparing allyl amines comprising:
(a) contacting allyl alcohol with ammonia in an ammonia:allyl alcohol molar ratio of from about 1:1 to 20:1 in the presence of a catalytically effective amount of a phosphorus containing substance which is not a phosphorus containing ligand complexed with a metal at a temperature from about 0° to 400° C. produce an allyl amine; and
(b) recovering the allyl amine.

15. The process of claim 14 wherein the phosphorus containing substance is boron phosphate.

16. The process of claim 14 wherein the phosphorus containing substance is orthophosphoric acid.

17. The process of claim 14 wherein the phosphorus containing substance is present in an amount from about 0.05 to about 10 mole % based upon the amount of allyl alcohol present.

* * * * *